(12) United States Patent
Burke et al.

(10) Patent No.: US 8,150,633 B2
(45) Date of Patent: Apr. 3, 2012

(54) SEAFOOD PHYSICAL CHARACTERISTIC ESTIMATION SYSTEM AND METHOD

(76) Inventors: Timothy A. Burke, Halifax (CA); Peter H. Gregson, Halifax (CA); Gleb J. Sekretta, Halifax (CA); Stephen J. F. Hankinson, Timberlea (CA)

(*) Notice: Subject to any disclaimer, the term of this patent is extended or adjusted under 35 U.S.C. 154(b) by 541 days.

(21) Appl. No.: 12/274,009

(22) Filed: Nov. 19, 2008

(65) Prior Publication Data

US 2009/0132174 A1    May 21, 2009

Related U.S. Application Data

(60) Provisional application No. 60/988,905, filed on Nov. 19, 2007.

(51) Int. Cl.
*G01N 33/48* (2006.01)
*G01F 11/30* (2006.01)
*G01R 23/00* (2006.01)

(52) U.S. Cl. ............ 702/19; 702/75; 702/104; 702/184; 324/668

(58) Field of Classification Search .................... 702/19, 702/71, 72, 75, 76, 82, 106, 107, 184, 187, 702/188; 73/597, 598, 602; 250/458.1; 324/226, 324/263, 663, 665, 668, 692; 426/2, 35, 426/108, 231, 389, 392, 398, 523; 436/2, 436/172; 452/161; 348/89
See application file for complete search history.

(56) References Cited

U.S. PATENT DOCUMENTS

| | | | |
|---|---|---|---|
| 3,735,247 A | 5/1973 | Harker | |
| 4,468,610 A | 8/1984 | Hanson | |
| 4,496,907 A | 1/1985 | Funk et al. | |
| 4,560,923 A | 12/1985 | Hanson | |
| 4,631,413 A | 12/1986 | Jensen et al. | |
| 4,758,778 A | 7/1988 | Kristinsson | |
| 4,908,703 A | 3/1990 | Jensen et al. | |
| 5,079,951 A | 1/1992 | Raymond et al. | |
| 5,223,796 A | 6/1993 | Waldman et al. | |
| 5,288,613 A | 2/1994 | Luong et al. | |
| 5,289,123 A | 2/1994 | Bublitz et al. | |
| 5,339,962 A | 8/1994 | Sommer, Jr. et al. | |
| 5,397,994 A | 3/1995 | Phare | |
| 5,426,373 A | 6/1995 | Diamond et al. | |
| 5,572,123 A | 11/1996 | Wikswo, Jr. et al. | |
| 5,625,147 A | 4/1997 | Miles et al. | |
| 6,132,303 A | 10/2000 | Buckhaven | |
| 6,228,404 B1 | 5/2001 | Eilert et al. | |

(Continued)

FOREIGN PATENT DOCUMENTS

CA    2310912    12/2000

(Continued)

*Primary Examiner* — John H Le

(57) ABSTRACT

Systems and methods for estimating a physical characteristic of a seafood product are provided. In one system, the estimate is based on a slope defined by a ratio of changes in peak resonant amplitude and frequency of an electromagnetic resonant circuit in loaded and unloaded states. In another system, a first probe of a plurality of probes is driven with a test signal when the plurality of probes is loaded by a seafood product and the estimate is based on received test signals at one or more of the other probes. In another system, the estimate is based on the loading effect of a seafood product on an electromagnetic resonant circuit, which is also used to read an ID from an RFID associated with the seafood product. The systems and methods may be used for individual specimens, or to determine an average estimate for multiple specimens at one time.

31 Claims, 6 Drawing Sheets

U.S. PATENT DOCUMENTS

| | | | |
|---|---|---|---|
| 6,265,882 B1 | 7/2001 | Madsen et al. | |
| 6,361,426 B1 | 3/2002 | Kragh | |
| 6,371,051 B1 | 4/2002 | Klein et al. | |
| 6,649,412 B1 | 11/2003 | Borggaard et al. | |
| 7,107,852 B2 | 9/2006 | Hutchins et al. | |
| 7,149,658 B2 * | 12/2006 | Kadaba | 702/184 |
| 7,164,749 B2 | 1/2007 | Schrock et al. | |
| 2002/0099454 A1 | 7/2002 | Gerrity | |
| 2002/0173041 A1 | 11/2002 | Canas et al. | |
| 2005/0155430 A1 | 7/2005 | Hutchins et al. | |
| 2005/0287252 A1 | 12/2005 | Schrock et al. | |
| 2006/0153271 A1 | 7/2006 | Hill et al. | |

FOREIGN PATENT DOCUMENTS

| | | |
|---|---|---|
| CA | 2510502 | 7/2004 |
| EP | 0 499 765 | 8/1992 |
| EP | 1 200 312 | 5/2002 |
| EP | 1 451 573 | 9/2004 |
| GB | 2 120 391 | 11/1983 |
| GB | 2 213 263 | 8/1989 |
| GB | 2 288 022 | 10/1995 |
| GB | 2 298 923 | 9/1996 |
| WO | WO 03/019174 | 3/2003 |
| WO | WO 2004/055504 | 7/2004 |
| WO | WO 2006/005335 | 1/2006 |
| WO | WO 2006/016824 | 2/2006 |
| WO | WO 2006/057990 | 6/2006 |
| WO | WO 2006/070169 | 7/2006 |

* cited by examiner

110 ↘

┌─────────────────────────────────────────────┐
│ Determine a reference peak resonant frequency │
│ ($F_{resonant\_ref}$) and reference peak resonant amplitude │ 112
│ ($A_{resonant\_ref}$) of an electromagnetic resonant circuit in │
│ an unloaded state │
└─────────────────────────────────────────────┘
                       ↓
┌─────────────────────────────────────────────┐
│ Determine a minimum peak resonant frequency │
│ ($F_{resonant\_min}$) and resonant peak amplitude ($A_{resonant\_min}$) │ 114
│ at $F_{resonant\_min}$ of the electromagnetic resonant circuit │
│ when loaded by a seafood product │
└─────────────────────────────────────────────┘
                       ↓
┌─────────────────────────────────────────────┐
│ Estimate a physical characteristic of the seafood │ 116
│ product as a function of a slope defined by: │
│ ($A_{resonant\_ref}$ − $A_{resonant\_min}$) / ($F_{resonant\_ref}$ − $F_{resonant\_min}$) │
└─────────────────────────────────────────────┘

FIG. 1

SEAFOOD PHYSICAL CHARACTERISTIC ESTIMATION SYSTEM AND METHOD

CROSS REFERENCE TO RELATED APPLICATIONS

The present patent application claims the benefit of U.S. Provisional Patent Application Ser. No. 60/988,905 filed on Nov. 19, 2007, the entire contents of which are incorporated herein by reference.

FIELD OF THE INVENTION

The invention pertains to the field of non-invasive electromagnetic sensing, and more particularly to sensing for estimation of one or more physical characteristics of seafood products.

BACKGROUND OF THE INVENTION

It is known that many aquatic invertebrates such as crustaceans go through a cycle of molting, in which an old hard shell is shed and a new larger soft shell is grown. Depending on the stage of the molting process, the crustacean's internal body, i.e., the "meat" portion of the lobster, may occupy a reduced part of the internal volume of the new shell as the internal body grows to occupy the new, larger shell. The internal structure of the crustacean, including its organs, meat and muscle, is undersized in proportion to its new shell after molting. In order to "fill out" this new, oversized shell, the crustacean takes on and retains water within its internal structure. As a result, inter-molt crustaceans (hard shell) generally produce high meat yields, while post-molt (soft shell) crustaceans generally produce very low meat yields.

Seafood is often an expensive food product for which a consumer pays a premium. In return, the consumer expects to receive a high quality product that reflects the price paid. For example, consumers will often pay a premium for larger crustaceans, in terms of weight and/or size, and the consumer will generally expect the size of the crustacean to correspond to the amount of meat yielded by the crustacean. However, due to the variance in the ratio of intracellular water to extracellular water in the shell cavity of the crustacean, i.e., the ratio of the amount of water stored in the muscle or "meat" of the crustacean to the amount of water stored outside of the muscle to "fill out" the shell, a larger post-molt crustacean may not yield any more meat than a smaller pre-molt or inter-molt crustacean.

Inter-molt crustaceans can often be identified by their hard shells and other external characteristics such as color. However, these measures are unreliable as a means to determine meat yields and are difficult to implement as non-invasive measures on a production line. Other attempts at sensing systems employing ultrasound or x-ray scanning systems have proven difficult to implement and failed to accurately distinguish between different shell hardnesses and/or different meat yields.

Beyond meatedness, the molt state of a crustacean can also be used as a "health" indicator that provides a seafood processor with the advantage of being able to assess anticipated mortality rates during storage.

Conventional meat yield sensing systems have relied on an assumed correlation between the refractive index (RI) of the blood of crustaceans and the stage of molt of a crustacean, and hence the meatedness of the lobster. However, while these methods may be fairly accurate at predicting meat yield, they require an invasive blood test of the crustacean and the use of a refractometer to determine the RI of the blood, which is impractical in a production plant setting at typical production rates.

In addition, conventional means of detecting meatedness are difficult to assess on live seafood product, at production speeds, because of varying pose/position of the crustacean under test.

SUMMARY OF THE INVENTION

The ability to identify, for example, lobsters with a high meat yield may allow seafood distributors or retailers to provide their customers with a greater level of confidence that a given lobster will have at least a minimum meat yield, and may also allow for a further sorting of lobsters into quality grades that are appropriate for different customers.

According to one aspect of the present invention, there is provided a method comprising: determining a minimum peak resonant frequency $F_{resonant\_min}$ and peak resonant amplitude $A_{resonant\_min}$ at $F_{resonant\_min}$ of an electromagnetic resonant circuit when loaded by a seafood product; and estimating a physical characteristic of the seafood product based on a slope defined by:

$$(A_{resonant\_ref} - A_{resonant\_min})/(F_{resonant\_ref} - F_{resonant\_min}),$$

where $F_{resonant\_ref}$ is a reference peak resonant frequency of the electromagnetic resonant circuit in an unloaded state, and $A_{resonant\_ref}$ is a reference peak resonant amplitude of the electromagnetic resonant circuit in the unloaded state.

In some embodiments, the method further comprises: determining the reference peak resonant frequency $F_{resonant\_ref}$ and the reference peak resonant amplitude $A_{resonant\_ref}$ of the electromagnetic resonant circuit in the unloaded state.

In some embodiments, the method further comprises: determining a weight of the seafood product, wherein estimating the physical characteristic comprises estimating the physical characteristic based on the slope and the weight of the seafood product.

In some embodiments, determining $F_{resonant\_ref}$ and $A_{resonant\_ref}$ comprises: applying a plurality of excitation frequencies to the electromagnetic resonant circuit in the unloaded state; measuring an amplitude of an output of the electromagnetic resonant circuit for each one of the excitation frequencies; determining $A_{resonant\_ref}$ as a peak amplitude of the measured amplitudes; and determining $F_{resonant\_ref}$ as the excitation frequency corresponding to the peak amplitude of the measured amplitudes.

In some embodiments, determining $F_{resonant\_ref}$ and $A_{resonant\_ref}$ comprises: maintaining a record of peak resonant amplitudes and frequencies in previous unloaded states; applying a plurality of excitation frequencies to the electromagnetic resonant circuit in the current unloaded state; measuring an amplitude of an output of the electromagnetic resonant circuit for each one of the excitation frequencies; determining $A_{resonant\_ref}$ as a rolling average of a number of the peak resonant amplitudes of the previous unloaded states and the peak amplitude of the current measured amplitudes; and determining $F_{resonant\_ref}$ as a rolling average of a number of the peak resonant frequencies of the previous unloaded states and the peak resonant frequency of the current measured amplitudes corresponding to the peak amplitude of the current measured amplitudes.

In some embodiments, the method further comprises: maintaining a database of $A_{resonant\_ref}$, $A_{resonant\_min}$, $F_{resonant\_ref}$ and $F_{resonant\_min}$ for each seafood product.

In some embodiments, the method further comprises: maintaining the estimated physical characteristic for each seafood product in the database.

In some embodiments, the method further comprises: performing linear regression on the slope to determine a linear relationship between the slope and the physical characteristic.

In some embodiments, the method further comprises: updating a webpage based on contents of the database.

In some embodiments, the method further comprises: determining a threshold as a boundary between quality grades; and determining a quality grade of the seafood product by comparing the slope to the threshold.

In some embodiments, determining the threshold comprises performing a data mining algorithm.

In some embodiments, the method further comprises: calibrating by: determining a slope for a calibration seafood product with a known physical characteristic; and adjusting a function for estimating the physical characteristic based on any discrepancy between the known physical characteristic and the physical characteristic estimate based on the determined slope.

In some embodiments, the seafood product comprises a plurality of specimens.

In some embodiments, the plurality of specimens are contained in a crate.

In some embodiments, the method further comprises: reading an ID from a Radio Frequency Identification (RFID) tag associated with the seafood product with the electromagnetic resonant circuit; and associating the ID of the RFID tag associated with the seafood product with information relating to the estimation of the physical characteristic of the seafood product.

In some embodiments, associating the ID of the RFID tag associated with the seafood product with information relating to the estimation of the physical characteristic of the seafood product comprises at least one of: transmitting, via the electromagnetic resonant circuit, information relating to the estimation of the physical characteristic of the seafood product to the RFID tag associated with the seafood product for storage on the RFID tag; and storing the information relating to the estimation of the physical characteristic of the seafood product in a database, such that the information is associated with the ID of the RFID tag.

In some embodiments, the method further comprises: reading the RFID tag associated with the seafood product to retrieve the information relating to the estimation of the physical characteristic of the seafood product associated with the RFID tag; and sorting the seafood product into one of at least two grades based on the information retrieved from the RFID tag.

According to another aspect of the present invention, there is provided a system comprising: a sensor comprising an electromagnetic resonant circuit; a controller, functionally connected to the electromagnetic resonant circuit, that: determines a minimum peak resonant frequency $F_{resonant\_min}$ and peak resonant amplitude $A_{resonant\_min}$ at $F_{resonant\_min}$ of the electromagnetic resonant circuit when the electromagnetic resonant circuit is loaded by a seafood product; and estimates a physical characteristic of the seafood product based on a slope defined by:

$$(A_{resonant\_ref} - A_{resonant\_min})/(F_{resonant\_ref} - F_{resonant\_min})$$

where $F_{resonant\_ref}$ is a reference peak resonant frequency of the electromagnetic resonant circuit in an unloaded state, and $A_{resonant\_ref}$ is a reference peak resonant amplitude of the electromagnetic resonant circuit in the unloaded state.

In some embodiments, the controller also determines the reference peak resonant frequency $F_{resonant\_ref}$ and the reference peak resonant amplitude $A_{resonant\_ref}$ of the electromagnetic resonant circuit in the unloaded state.

In some embodiments, the system further comprises: a weight scale, functionally connected to the controller, that determines a weight of the seafood product, wherein the controller estimates the physical characteristic based on the slope and the weight of the seafood product.

In some embodiments, the controller comprises a variable frequency source, and wherein the controller determines $F_{resonant\_ref}$ and $A_{resonant\_ref}$ by: controlling the variable frequency source to apply a plurality of excitation frequencies to the electromagnetic resonant circuit in the unloaded state; measuring an amplitude of an output of the electromagnetic resonant circuit for each one of the excitation frequencies; determining $A_{resonant\_ref}$ as a peak amplitude of the measured amplitudes; and determining $F_{resonant\_ref}$ as the excitation frequency corresponding to the peak amplitude of the measured amplitudes.

In some embodiments, the controller: maintains a record of peak resonant amplitudes and frequencies in previous unloaded states; determines $A_{resonant\_ref}$ as a rolling average of a number of the peak resonant amplitudes of the previous unloaded states and the peak amplitude of the current measured amplitudes; and determines $F_{resonant\_ref}$ as a rolling average of a number of the peak resonant frequencies of the previous unloaded states and the peak resonant frequency of the current measured amplitudes corresponding to the peak amplitude of the current measured amplitudes.

In some embodiments, the system further comprises: a server having a database in communication with the controller, wherein the controller stores a record in the database of the estimated physical characteristic, $A_{resonant\_ref}$, $A_{resonant\_min}$, $F_{resonant\_ref}$ and $F_{resonant\_min}$ for each seafood product.

In some embodiments, the server further comprises: an interface comprising a webpage that is updated based on contents of the database.

In some embodiments, the electromagnetic resonant circuit comprises: two substantially co-planar plates separated by a gap; an inductor having a first end and a second end respectively functionally connected to the two substantially co-planar plates; a tickler coil inductively coupled to the inductor; and a sense coil inductively coupled to the inductor, wherein the controller applies a plurality of excitation frequencies to the tickler coil and determines $F_{resonant\_min}$ and $A_{resonant\_min}$ based on an output of the sense coil when the electromagnetic resonant circuit is loaded by the seafood product.

In some embodiments, the system further comprises: a biologist station console functionally connected to the controller, the biologist station console allowing a user to enter a known physical characteristic of a calibration seafood product, wherein the controller: determines a slope for the calibration seafood product with the known physical characteristic; and adjusts a function for estimating the physical characteristic based on any discrepancy between the known physical characteristic and the physical characteristic estimate based on the determined slope.

In some embodiments, the electromagnetic resonant circuit comprises three or more substantially planar plates separated by gaps.

In some embodiments, the three or more substantially planar plates define a volume.

In some embodiments, the seafood product comprises a plurality of specimens.

In some embodiments, the electromagnetic resonant circuit is part of a Radio Frequency Identification (RFID) reader.

In some embodiments, the controller is configured to perform at least one of the following steps: transmit, via the electromagnetic resonant circuit, information relating to the estimation of the physical characteristic of the seafood product to an RFID tag associated with the seafood product; and store the information relating to the estimation of the physical characteristic of the seafood product in a database, such that in the database the information is associated with an ID of the RFID tag associated with the seafood product.

In some embodiments, the system further comprises: a second RFID reader comprising a second electromagnetic resonant circuit configured to read the RFID tag associated with the seafood product to retrieve the information relating to the estimation of the physical characteristic of the seafood product; and a grader, functionally connected to the RFID reader, configured to sort the seafood product into one of at least two grades based on the information retrieved from the RFID tag.

In some embodiments, the information relating to the estimation of the physical characteristic of the seafood product comprises a grade of the seafood product, and wherein sorting the seafood product comprises sorting the seafood product based on the grade of the seafood product stored on the RFID tag.

According to yet another aspect of the present invention, there is provided a method comprising: driving a first probe of a plurality of probes with a test signal, when the plurality of probes is loaded by a seafood product; measuring received test signals at one or more other probes of the plurality of probes; and estimating a physical characteristic of the seafood product based on the received test signals.

In some embodiments, driving comprises sequentially driving each of the probes of the plurality of probes with the test signal.

In some embodiments, measuring comprises measuring the received signals with each of the other probes of the plurality of probes.

In some embodiments, the method further comprises: determining calibration references by: driving the first probe of the plurality of probes with a test signal, when the plurality of probes is unloaded; and measuring received test signals at the one or more other probes of the plurality of probes, wherein estimating comprises estimating based on the calibration references and the test signals received when the plurality of probes is loaded by the seafood product.

In some embodiments, estimating comprises estimating the physical characteristic as a function of a difference in magnitude between the received test signals and the calibration references.

In some embodiments, driving comprises driving the first probe with a plurality of test signals, each test signal corresponding to one of a plurality of frequencies.

In some embodiments, the seafood product comprises a plurality of specimens, and wherein estimating a physical characteristic of the seafood product comprises estimating an average physical characteristic of the plurality of specimens.

In some embodiments, the method further comprises sorting the seafood product into one of at least two grades based on the estimated physical characteristic.

In some embodiments, the method further comprises contacting the plurality of probes to the seafood product.

In some embodiments, the seafood product comprises a lobster, and contacting the plurality of probes to the seafood product comprises contacting the plurality of probes to an underside of a tail of the lobster.

In some embodiments, measuring received test signals at one or more other probes of the plurality of probes comprises: measuring relative impedance of tissue occupying space between the first probe and the one or more other probes of the plurality of probes; and generating a profile of tissue impedance along the plurality of probes, wherein estimating a physical characteristic of the seafood product based on the received test signals comprises estimating the physical characteristic based on a gradient of the profile.

According to still another aspect of the present invention, there is provided a system comprising: a sensor comprising a plurality of probes; a controller, functionally connected to the sensor, that: drives a first probe of the plurality of probes with a test signal, when the plurality of probes is loaded by a seafood product; measures received test signals at one or more other probes of the plurality of probes; and estimates a physical characteristic of the seafood product based on the received test signals.

In some embodiments, the plurality of probes comprises a plurality of plates defining a volume, and wherein the controller drives a first plate of the plurality of plates with the test signal when the plurality of plates is loaded by the seafood product within the volume.

In some embodiments, the seafood product comprises a plurality of specimens.

In some embodiments, the plurality of specimens are contained in a crate.

In some embodiments, the controller determines calibration references by: driving the first probe of the plurality of probes with a test signal, when the plurality of probes is unloaded; and measuring received test signals at the one or more other probes of the plurality of probes, wherein estimating comprises estimating based on the calibration references and the test signals received when the plurality of probes is loaded by the seafood product.

In some embodiments, the controller drives each of the plurality of probes with the test signal individually, and while each probe is driven, measures the received test signals at the one or more other test probes.

In some embodiments, the controller comprises a variable frequency source that generates the test signal, and wherein the test signal comprises a plurality of test signals, each test signal having one of a plurality of frequencies.

In some embodiments, the plates are u-shaped, and the volume comprises a u-shaped volume.

In some embodiments, the plurality of plates comprises four u-shaped plates.

In some embodiments, the system further comprises: an electromagnetic shield surrounding an outer periphery of the plurality of plates that substantially confines electromagnetic fields generated by the plurality of plates to the volume defined by the plurality of plates.

In some embodiments, the plurality of plates are mounted on non-conducting standoffs that provide galvanic isolation between the shield and the plurality of plates.

In some embodiments, the seafood product comprises a lobster, and wherein the plurality of probes are arranged for contact on an underside of a tail of the lobster.

In some embodiments, the controller: measures relative impedance of tissue occupying space between the first probe and the one or more other probes of the plurality of probes; generates a profile of tissue impedance along the plurality of probes; and estimates the physical characteristic of the seafood product based on a gradient of the profile.

According to a further aspect of the present invention, there is provided a handheld device for estimating a physical characteristic of a seafood product comprising the system according to the aspect of the present invention described above.

According to yet another aspect of the present invention, there is provide a method comprising: reading an ID from a Radio Frequency Identification (RFID) tag associated with a seafood product with an electromagnetic resonant circuit; determining a loading effect of the seafood product on the electromagnetic resonant circuit when loaded by the seafood product; estimating a physical characteristic of the seafood product based on the loading effect of the seafood product; and associating the ID from the RFID tag associated with the seafood product with information relating to the estimation of the physical characteristic of the seafood product.

In some embodiments, associating the ID from the RFID tag associated with the seafood product with information relating to the estimation of the physical characteristic of the seafood product comprises at least one of: transmitting, via the electromagnetic resonant circuit, the information relating to the estimation of the physical characteristic of the seafood product to the RFID tag associated with the seafood product for storage on the RFID tag; and storing the information relating to the estimation of the physical characteristic of the seafood product in a database, such that the information is associated in the database with the ID of the RFID tag In some embodiments, the electromagnetic resonant circuit comprises an antenna, and wherein determining the loading effect of the seafood product on the electromagnetic resonant circuit comprises at least one of: determining a change in impedance of the antenna between an unloaded state and when loaded by the seafood product; determining a phase angle of a standing wave ratio (SWR) of the antenna; and determining a change in the gain of the antenna between the unloaded state and when loaded by the seafood product.

In some embodiments, the method further comprises: reading the RFID tag to retrieve the information relating to the estimation of the physical characteristic of the seafood product from the RFID tag associated with the seafood product; and sorting the seafood product into one of at least two grades based on the information retrieved from the RFID tag.

In some embodiments, the information relating to the estimation of the physical characteristic of the seafood product comprises a grade of the seafood product; and sorting the seafood product comprises sorting the seafood product based on the grade of the seafood product stored on the RFID tag.

In some embodiments, operating frequency of the electromagnetic resonant circuit is in a range of about 1 MHz to about 100 MHz.

In some embodiments, the method further comprises: determining a weight of the seafood product, wherein estimating the physical characteristic comprises estimating the physical characteristic based on the loading effect and the weight of the seafood product.

In some embodiments, the method further comprises: maintaining the database such that for each seafood product the database maintains a record of the ID of the RFID tag associated with the seafood product and at least one of: the loading effect of the seafood product and the estimated physical characteristic of the seafood product.

In some embodiments, the method further comprises: performing linear regression on the loading effect to determine a linear relationship between the loading effect and the physical characteristic.

In some embodiments, the method further comprises: determining a threshold as a boundary between quality grades; and determining a quality grade of the seafood product by comparing the loading effect to the threshold.

In some embodiments, determining the threshold comprises performing a data mining algorithm.

In some embodiments, the method further comprises: calibrating by: determining a loading effect on the electromagnetic resonant circuit for a calibration seafood product with a known physical characteristic; and adjusting a function for estimating the physical characteristic based on any discrepancy between the known physical characteristic and the physical characteristic estimate based on the determined loading effect for the calibration seafood product.

In some embodiments, the seafood product comprises a plurality of specimens.

According to still another aspect of the present invention, there is provided a system comprising: an electromagnetic resonant circuit; a controller, functionally connected to the electromagnetic resonant circuit, that: reads an ID from a Radio Frequency Identification (RFID) tag associated with a seafood product with the electromagnetic resonant circuit; determines a loading effect of the seafood product on the electromagnetic resonant circuit when the electromagnetic resonant circuit is loaded by the seafood product; estimates a physical characteristic of the seafood product based on the determined loading effect of the seafood product; and associates the ID from the RFID tag associated with the seafood product with information relating to the estimation of the physical characteristic of the seafood product.

In some embodiments, the controller associates the ID from the RFID tag associated with the seafood product with information relating to the estimation of the physical characteristic of the seafood product by performing at least one of the following steps: transmitting, via the electromagnetic resonant circuit, the information relating to the estimation of the physical characteristic of the seafood product to the RFID tag associated with the seafood product; and storing the information relating to the estimation of the physical characteristic of the seafood product in a database, such that the information is associated in the database with the ID of the RFID tag.

In some embodiments, the electromagnetic resonant circuit comprises an antenna, and wherein the controller determines the loading effect of the seafood product on the electromagnetic resonant circuit by determining at least one of: a change in impedance of the antenna between an unloaded state and when loaded by the seafood product; a phase angle of a standing wave ratio (SWR) of the antenna; and a change in the gain of the antenna between the unloaded state and when loaded by the seafood product.

In some embodiments, the system further comprises: an RFID reader comprising a second electromagnetic resonant circuit configured to read the RFID tag associated with the seafood product to retrieve the information relating to the estimation of the physical characteristic of the seafood product; and a grader, functionally connected to the RFID reader, configured to sort the seafood product into one of at least two grades based on the information retrieved from the RFID tag.

In some embodiments, the information relating to the estimation of the physical characteristic of the seafood product comprises a grade of the seafood product; and sorting the seafood product comprises sorting the seafood product based on the grade of the seafood product stored on the RFID tag.

In some embodiments, operating frequency of the electromagnetic resonant circuit is in a range of about 1 kHz to about 100 MHz.

In some embodiments, the system further comprises: a weight scale, functionally connected to the controller, configured to determine a weight of the seafood product, wherein the controller estimates the physical characteristic by estimating the physical characteristic based on the loading effect and the weight of the seafood product.

In some embodiments, the system further comprises: the database in communication with the controller that for each seafood product maintains a record of the ID of the RFID tag relating to the seafood product and at least one of: the loading effect of the seafood product and the estimated physical characteristic of the seafood product.

In some embodiments, the controller performs linear regression on the loading effect to determine a linear relationship between the loading effect and the physical characteristic.

In some embodiments, the controller: determines a threshold as a boundary between quality grades; and determines a quality grade of the seafood product by comparing the loading effect to the threshold.

In some embodiments, the controller performs a data mining algorithm to determine the threshold.

In some embodiments, the controller comprises a variable frequency source.

In some embodiments, the system further comprises: a biologist station console functionally connected to the controller, the biologist station console allowing a user to enter a known physical characteristic of a calibration seafood product, wherein the controller: determines the loading effect of the calibration seafood product with the known physical characteristic on the electromagnetic resonant circuit; and adjusts a function for estimating the physical characteristic based on any discrepancy between the known physical characteristic and the physical characteristic estimate based on the determined loading effect of the calibration seafood product.

In some embodiments, the seafood product comprises a plurality of specimens.

Other aspects and features of the present invention will become apparent, to those ordinarily skilled in the art, upon review of the following description of the specific embodiments of the invention.

BRIEF DESCRIPTION OF THE DRAWINGS

Embodiments of the invention will now be described in greater detail with reference to the accompanying diagrams, in which:

FIG. 1 is a flowchart of an example of a method in accordance with an embodiment of the invention;

DETAILED DESCRIPTION

Figure 2:
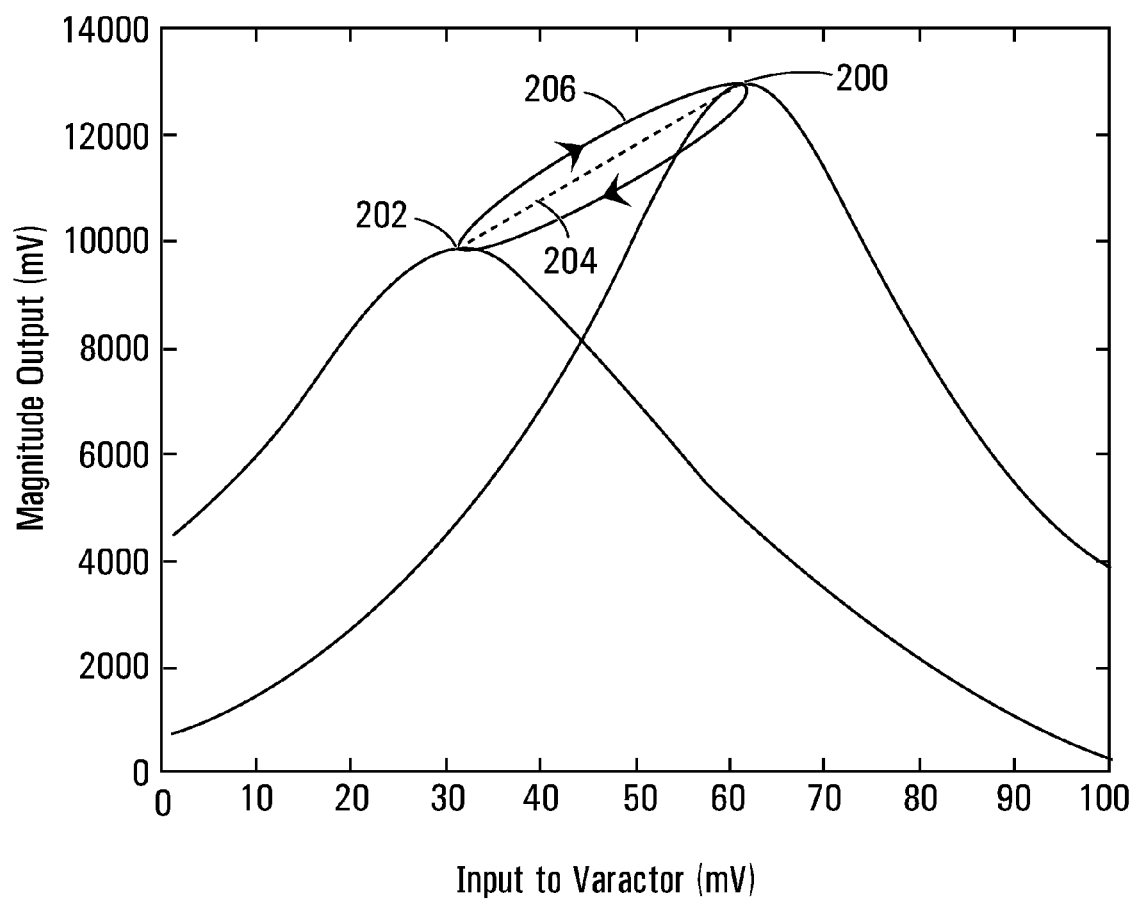
FIG. 2 is a plot of the frequency response of an electromagnetic resonant circuit in an unloaded state and a loaded state in accordance with an embodiment of the present invention.

Various systems and methods for non-invasive estimation of one or more physical characteristics of seafood products such as lobsters and other crustaceans, such as scallops, crabs, mussels and sea urchins are provided. Embodiments of the present invention may provide for online physical characteristic estimation at typical production speeds and/or grading and separation of low and high meat yield seafood products at typical production rates at any stage of seafood processing. For example, some embodiments of the present invention are used at typical production rates of 90 crustaceans per minute, with peak rates of close to 120 crustaceans per minute. Other embodiments may be suitable for production rates higher or lower than these typical average and peak rates.

Some embodiments of the invention exploit the fact that the resonant frequency and amplitude of an electromagnetic resonant circuit will change when the circuit is "loaded" with an object that interacts with the electromagnetic field generated by the circuit. That is, when an object, such as a lobster with a particular amount of water held within its internal structure, is exposed to the electromagnetic field generated by the circuit, the electromagnetic field will be altered by interaction with the object, and the resonant frequency and amplitude of the oscillation in the loaded circuit will change depending on the properties of the object.

In general, any additional loading of the resonant circuit will result in a reduction of both the resonant frequency and amplitude of the oscillation in the circuit.

In some embodiments, the phase of a signal at the resonant frequency of the electromagnetic resonant circuit, relative to the phase of an input signal used to drive the circuit may be used to facilitate estimation of a property of a seafood product under test, as the properties of a seafood product, such as tissue water content, may affect the phase of an electromagnetic resonant circuit when the circuit is loaded with the seafood product.

Salt water is a relatively good conductor of electromagnetic energy, and therefore an object composed of a relatively high percentage of salt water may load the circuit, i.e., change the impedance of the circuit and hence the resonant amplitude and frequency, more than an object with a relatively low percentage of salt water. Accordingly, the change in resonant frequency and amplitude of a resonant circuit in a loaded and an unloaded state may indicate the water content of the object that is presented as a load to the circuit.

A post-molt lobster will have a higher ratio of extracellular water to intracellular water in its internal structure compared to that of an inter-molt or pre-molt lobster due to the amount of water retained by a post-molt lobster within the new soft shell to fill it out. At certain frequencies, extracellular water will more easily conduct electricity compared to intracellular water, so a lobster with a high ratio of extracellular water to intracellular water (a post-molt lobster) will present a different load to a resonant circuit than a lobster with a lower ratio (an inter-molt or pre-molt lobster).

RFID readers and tags operate over a wide range of frequencies, however several of these frequencies are within a range, as described herein, that may be suitable to detect meat yield in seafood products, such as lobsters or other crustaceans.

In some embodiments, a Radio Frequency Identification (RFID) tag is associated with the seafood product under test, and an electromagnetic resonant circuit is implemented as part of an RFID reader that is operable to estimate a physical characteristic of the seafood product based on the loading effect of the seafood product on the electromagnetic resonant circuit and to transmit information relating to the estimated physical characteristic to the RFID tag associated with the seafood product. The information relating to the estimated physical characteristic transmitted to the RFID tag may then be retrieved from the RFID tag by RFID readers at later stages of processing, without requiring that the later RFID readers be operable to estimate the physical characteristic, as they can simply retrieve the information from the tag.

In some embodiments, rather than storing the information relating to the estimated physical characteristic on the RFID tag, the information may be stored in a database and associated with the ID of the RFID tag, so that RFID readers at later stage of processing can read the ID of the RFID tag and retrieve the information relating to the estimated physical characteristic from the database using the ID of the RFID tag. In these embodiments, the RFID may not have memory for storing the information relating to the estimated physical characteristic.

In some embodiments, the information relating to the estimated physical characteristic may be both stored in a database and transmitted to the RFID tag for storage on the tag.

In some embodiments, for example, a lobster is tagged with an RFID tag in the form of a passive tag with some on-chip memory, for example. When an RFID reader that includes the electromagnetic resonant circuit interrogates the tag, it receives information about the identity of that lobster, but some of the energy will be absorbed by the tissue of the lobster, thereby producing a loading effect on the electromagnetic resonant circuit that is a part of the RFID reader, for example, resulting in a change of impedance in the circuit that is detectable from the RFID reader. This change in impedance within the field of the RFID reader can be sensed and used to estimate a physical characteristic of the lobster, for example the relative meat yield of the lobster. This information relating to the estimate of the physical characteristic can then be pushed by the RFID reader to the on-chip memory on the passive RFID tag attached to that lobster. In these embodiments, the RFID tag carries both information relative to the identification of the lobster as well as its estimated meat yield with no additional sensing hardware (other than the RFID reader).

It should be understood that the electromagnetic resonant circuit that is included as part of an RFID reader as described herein can be used as a source of radio frequency (RF) energy that can be loaded by a seafood product. The loading effect of the seafood product on the resonant circuit may be used to estimate a physical characteristic of the seafood product using the "slope" algorithm as described herein, or any algorithm in which the loading effect of the seafood product can be correlated with a physical characteristic.

An example of a method for non-invasive estimation of a physical characteristic of a seafood product in accordance with an embodiment of the present invention will now be described with reference to FIG. 1.

The method 110 begins at step 112, in which a reference peak resonant frequency $F_{resonant\_ref}$ and reference peak resonant amplitude $A_{resonant\_ref}$ of an electromagnetic resonant circuit in an unloaded state are determined. This step may be performed as an initial calibration step with the result being stored for subsequent access, periodically during operation of an estimation system, or each time the physical characteristic is to be estimated, for example.

In step 114, a minimum peak resonant frequency $F_{resonant\_min}$ and peak resonant amplitude $A_{resonant\_min}$ at $F_{resonant\_min}$ of the electromagnetic circuit are determined when the circuit is loaded by a seafood product, such as a lobster.

In step 116, an estimate of a physical characteristic of the seafood product is determined as a function of a slope defined by:

$$(A_{resonant\_ref} - A_{resonant\_min})/(F_{resonant\_ref} - F_{resonant\_min}). \quad (1)$$

The physical characteristic may include the refractive index and/or meat yield of the seafood product, for example.

In some embodiments, $F_{resonant\_ref}$ and $A_{resonant\_ref}$ are determined by sequentially applying a plurality of excitation frequencies to the resonant circuit while it is unloaded and measuring the amplitude and frequency of an output of the resonant circuit for each excitation frequency to determine the peak amplitude and frequency, i.e., the resonant frequency and resonant amplitude.

Similarly, in some embodiments, $F_{resonant\_min}$ and $A_{resonant\_min}$ are determined by applying a plurality of excitation frequencies to the resonant circuit while it is loaded with the seafood product and measuring the amplitude and the frequency of the output of the resonant circuit for each of the excitation frequencies. The plurality of excitation frequencies may be applied to the circuit multiple times while the seafood product is exposed to the electromagnetic field generated by the circuit. For example, the seafood product may be moving on a processing plant belt so that it passes through the electromagnetic field generated by the resonant circuit so that the orientation and location of the seafood product relative to the electromagnetic field of the resonant circuit is changing while the plurality of excitation frequencies are being applied. Applying the plurality of excitation frequencies multiple times may allow for a more accurate determination of the minimum resonant frequency $F_{resonant\_min}$.

In some embodiments, the method 110 further comprises reading an ID from a Radio Frequency Identification (RFID) tag associated with the seafood product with the electromagnetic resonant circuit and storing information relating to the estimation of the physical characteristic of the seafood product.

In some embodiments, storing the information relating to the estimation of the physical characteristic comprises storing the information in a data base and/or transmitting the information to the RFID tag associated with the seafood product for storage on the RFID tag.

In some embodiments, at a later stage of processing, an RFID reader reads the RFID tag associated with the seafood product, to thereby retrieve the ID of the RFID tag and/or the information relating to the estimation of the physical characteristic of the seafood product from the RFID tag. The seafood product is sorted into one of at least two grades based on the information retrieved from the RFID tag in some embodiments.

Although only one cycle of the method 110 is shown in FIG. 1, the illustrated operations may be repeated as lobsters pass an estimation system on a production line. Other embodiments may include additional operations that have not been explicitly shown, such as grading and/or sorting operations based on meat yield estimates.

FIG. 2 provides a plot of the frequency response of an electromagnetic resonant circuit in an unloaded state and in a loaded state when loaded by a lobster or other object in accordance with an embodiment of the present invention. In the plot shown in FIG. 2, the x-axis represents a varactor control voltage for a varactor-controlled oscillator. Adjusting the varactor control voltage adjusts the oscillation frequency of a varactor-controlled oscillator in some embodiments of the invention. Accordingly, each of the illustrated varactor control voltages represents an oscillation frequency of an input of the electromagnetic resonant circuit.

The reference resonant peak 200 is decreased in amplitude and frequency to a minimum resonant peak 202 when the resonant circuit is loaded by the lobster. In the plot shown in FIG. 2, the plurality of excitation frequencies are applied multiple times while the lobster is passed through the electromagnetic field of the resonant circuit. The peak resonant frequency for each application of the plurality of excitation frequencies falls on the path 206 between reference resonant peak 200 and the minimum resonant peak 202, because the position of the lobster impacts its effect on the resonance of the circuit. The slope 204 defined by (1) between the reference resonant peak 200 and the minimum resonant peak 202 can be used as described herein to estimate the physical characteristic of the lobster.

It should be noted that the example plot shown in FIG. 2 is for illustrative purposes only. Different frequency responses may be observed, for example, for different resonant circuits operated under different conditions and/or for different objects loading a resonant circuit.

While the units for the y-axis of FIG. 2 are shown as mV, i.e., the output voltage of the resonant circuit, more generally any measurement that corresponds to a change in resonant frequency and magnitude of the resonant circuit in an unloaded and a loaded state can be used, as the calculated slope output is a relative measure between lobsters or other seafood products under test. For example, in some embodiments, analog to digital converter (ADC) counts may be used, where there are a specific number of ADC counts per volt.

The plurality of excitation frequencies may be selected on either side of the resonant frequency of the unloaded resonant circuit so that the resonant frequency of the unloaded resonant circuit falls within the range of excitation frequencies defined by the plurality of excitation frequencies.

In general, the range of frequencies defined by the plurality of excitation frequencies is selected to include the range of minimum peak resonant frequencies $F_{resonant\_min}$ resulting from the normal physical variation in the physical characteristic of a particular seafood product.

In some embodiments, a scanning frequency window of approximately 750 kHz to 1 MHz about the unloaded resonant frequency is sufficient to define an unloaded peak resonant amplitude and frequency and capture the shift in resonance when loaded. This range is an implementation specific detail and the foregoing range is provided merely as an example.

If the seafood product causes the minimum peak resonant frequency $F_{resonant\_min}$ to fall outside of the range of excitation frequencies, $F_{resonant\_min}$ may not be accurately determined, and the determination of the slope and hence the estimation of the physical characteristic may be inaccurate. The range of the plurality of excitation frequencies may be selected by running one or more sample seafood products through the measurement process to ensure that the range of excitation frequencies includes the minimum resonant peak frequencies of the sample seafood product(s).

The resonant circuit may be designed to have an unloaded resonant frequency that is chosen based on the particular electrical properties of the seafood product that is to be measured. For example, in some embodiments, a resonant circuit with a resonant peak close to 20 MHz in air may be used for lobsters. However, there is a broad range of frequencies in which low and high meated crustaceans, such as lobsters, appear to have different impedances. These differences in impedances will result in a different shift in resonance for low and high meated crustaceans, and therefore can be used to evaluate meatedness. For lobsters, resonant peaks as low as 75 kHz and as high as 100 MHz, may be used in some embodiments. The impact of using different resonant frequencies has to do with the impedance of intra/extracellular water of the crustacean resulting in flow path differences of current through the tissue/water of the crustacean at different frequencies.

In some embodiments, a "calibration" step is performed in which a plurality of sample lobsters are run through the method shown in FIG. 1 and then linear regression is used on the data from this sample population to determine a linear relationship between the slope determined by (1) and the physical characteristic. The use of linear regression techniques for processing data is described, for example, in Walpole, R. E., Myers, R. H., "Probability and Statistics for Engineers and Scientists," 5$^{th}$ Ed., New York, 1993. Other techniques may also or instead be used.

In some embodiments, a threshold slope is determined and seafood products having a slope above the threshold are determined to be "well-meated" product, while seafood products having a slope below the threshold are determined to be "low meat yield" product. The threshold may thus be used to separate lobsters into one of two "grades".

Other embodiments may use two thresholds: a lower threshold and an upper threshold. Seafood products having a slope above the upper threshold are determined to be "high meat yield" product, while seafood products having a slope between the lower threshold and the upper threshold are determined to be "medium meat yield" product, and seafood products having a slope below the lower threshold are determined to be "low meat yield" product.

As will be apparent, a number of thresholds may be chosen to implement virtually any desired grading or sorting "granularity".

The threshold or thresholds may be weight/size dependent. For example, lobsters are commonly categorized based on weight in to categories, such as canners, chix, quarters and selects. The threshold or thresholds for each of the categories may be different, since the relationship between the slope determined by (1) and the physical characteristic may very depending on the physical size/weight of the lobster.

In some embodiments, the reference peak resonant frequency $F_{resonant\_ref}$ and the reference peak resonant amplitude $A_{resonant\_ref}$ are determined based on a rolling average of a particular number of unloaded resonant frequency and amplitude measurements. For example, $F_{resonant\_ref}$ and $A_{resonant\_ref}$ may be the average of five measurements of the unloaded peak resonant frequency and amplitude.

Figure 3:
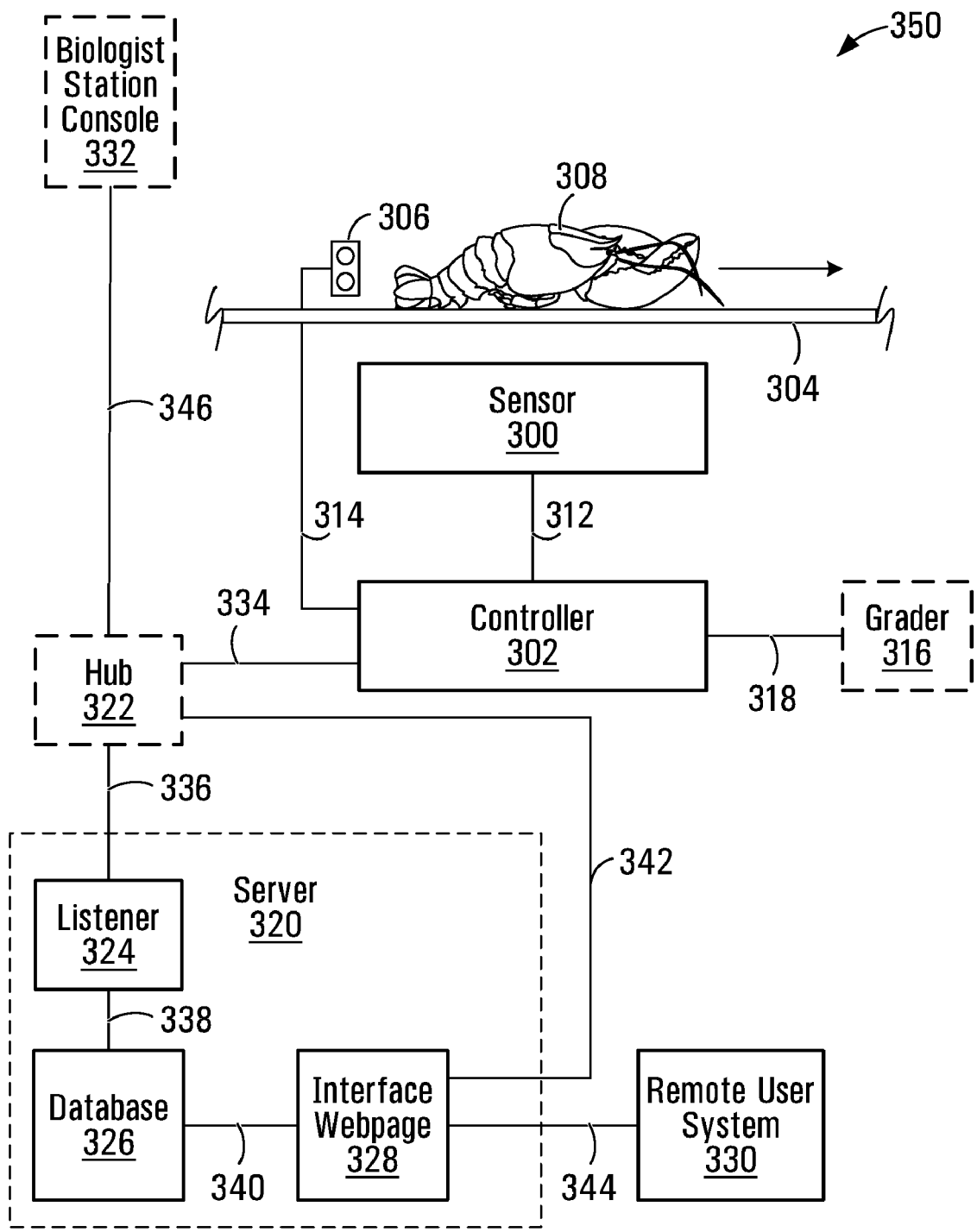
FIG. 3 is a block diagram of a system in accordance with an embodiment of the present invention.

FIG. 3 is an illustration of a block diagram of a system 350 in accordance with an embodiment of the present invention. It should be appreciated that the system 350 is intended solely for the purposes of illustration, and that other embodiments may include further, fewer, or different components interconnected in a similar or different manner than explicitly shown.

The system 350 includes a sensor 300 functionally connected to a controller 302 at 312.

The sensor 300 is located beneath and in close proximity to a processor belt 304 that carries a lobster 308 on its top surface in the example shown, although other arrangements are also possible.

In some embodiments, belt 304 is made of plastic, such as high density polyethylene (HDPE) with no metal content, as metal may interfere with sensor 300.

Salt water may also interfere with the measurements taken by sensor 300, i.e. salt water may reduce the impedance presented by belt 304, and therefore in some embodiments belt 304 is rinsed continuously with fresh water to maintain a relatively constant impedance.

A trigger 306 is located near the top surface of the belt 304 before the sensor 300 such that the passage of the lobster 308 on the belt 304 will trip the trigger 306. The trigger 306 is functionally connected to the controller 302 at 314.

In some embodiments, the trigger 306 includes an optical trigger. In general, the trigger 306 may be any type of sensor that detect the arrival of a lobster or other seafood product at a location ahead of the sensor 300. Although shown separately in FIG. 3, the trigger 306 could potentially be integrated into a single device with the controller 302 and/or the sensor 300.

The controller 302 has an output 318 that is functionally connected to a grader 316 that is located downstream of the sensor 300 with respect to the direction of the belt 304.

In some embodiments, the system 350 also includes a hub 322 that is functionally connected to the controller 302 at 334. The hub 322 is also functionally connected to a biologist station console 332 at 346 and to a server 320 at 336 and 342.

In some embodiments, the server 320 includes a listener 324, a database 326 and an interface 328. The listener 324 is functionally connected to the hub 322 at 336, and is also functionally connected to the database 326 at 338. The interface 328 is functionally connected to the database 326 at 340, and may be functionally connected to the hub 322 through the output 342 of the server 320.

The Listener 324 may be implemented as a software algorithm that manages data transfer from biologist station console 332 and controller 302, and stores the data in database 326, for instance.

In some embodiments, the interface 328 of the server 320 is implemented as a webpage such as a dynamic personal home page (PHP) webpage.

In some embodiments, a remote user system 330 is functionally connected to the interface 328 of the server 320 at 344.

In operation, as the lobster 308 is moved along by the belt 304, the trigger 306 is tripped by the lobster 308 prior to reaching the sensor 300. The trigger 306 signals the controller 302 through an output at 314 that the lobster 308 is approaching the sensor 300. The controller 302 determines a reference peak resonant frequency $F_{resonant\_ref}$ and amplitude $A_{resonant\_ref}$ of the sensor while the sensor is in an unloaded state, by driving an input of the sensor at 312 with a plurality of excitation frequencies and measuring an amplitude of an output of the sensor at 312 at each of the excitation frequencies. Although shown as a single connection 312 in FIG. 3, a separate input and output may be provided between the sensor 300 and the controller 302.

The reference peak and amplitude need not necessarily be determined by the controller 302 each time the trigger 306 detects a lobster 308 approaching the sensor 300. For example, the controller 302 might determine its references every few minutes. The references could then be stored in a memory (not shown) functionally connected to the controller 302 and accessed by the controller 302 until new references are to be determined.

As the lobster 308 passes over the sensor 300 on the belt 304, the excitation frequencies are applied again at least once to determine the minimum peak resonant frequency $F_{resonant\_min}$ and amplitude $A_{resonant\_min}$.

The slope defined by (1) may then be used to estimate a physical characteristic such as meat yield of the lobster 308. The slope and/or the physical characteristic may be passed on by the controller 302 through an output at 318 to the grader 316 for sorting purposes. The physical characteristic of the lobster 308 may be estimated indirectly by first using a linear regression of the slope defined by (1) vs. RI to determine the RI of the lobster. Correlation between RI and meat yield is quite strong (in some cases the correlation between RI and meat yield is r~0.93). Therefore, in some embodiments, when the physical characteristic of concern is meat yield, a threshold for distinguishing between grades of meat yield may be based on RI alone.

The proximity of the sensor 300 to the lobster 308 can affect the quality of measurements that can be made. For example, if the sensor 300 is located too far from the lobster 308, the signal to noise ratio of the output at 312 of the sensor will be low, since the lobster 308 may pass through only the fringes of the electromagnetic field of the sensor 300. Furthermore, the consistency of the distance between the lobster 308 and the sensor 300 may be important, because differences in this distance can cause variations in the measurements.

In some embodiments, the sensor 300 is located within one or two inches of the bottom of the belt 304.

Figure 4:
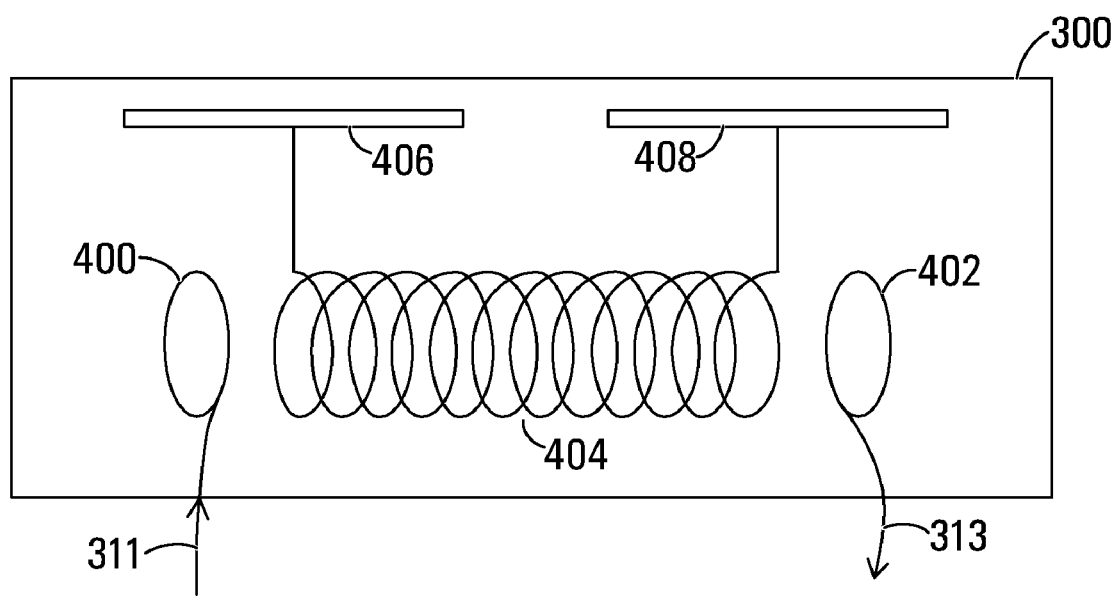
FIG. 4 is a schematic of an electromagnetic resonant circuit in accordance with an embodiment of the invention.

In general, the distance between the sensor 300 and the belt 304 is an implementation specific detail that may depend, for example, on the sensitivity of the sensor 300, the material of the belt 304, the state of the belt 304 (for example: salty, wet, dirty), the gap size between the neighbouring co-planar plates (406 and 408) for a sensor such as that illustrated in FIG. 4, and/or the seafood product under test.

Accordingly, oscillations in the processing belt 304 may cause measurement errors. For this reason, a "chute-style" system may be instead used, where the lobster 308 slides down a rigid chute that is a set distance from the sensor 300, which could eliminate the errors associated with oscillations of the belt 304.

In some embodiments, a tensioning roller may be used underneath the belt 304 to maintain a relatively constant tension in the belt to reduce oscillations and static variations in the distance between the belt 304 and the sensor 300.

In addition, inconsistencies in the electrical properties of the belt along its length can affect the measurements. An old belt that is partially wetted with salt water can cause large variations in the measurements, for example.

In some embodiments, the belt 304 is sprayed and rinsed with fresh water to reduce inconsistencies in the belt conditions.

In some embodiments, the system includes a weight scale that measures the weight of the lobster 308 and reports the weight to the controller 302 for use in estimating the physical characteristic of the lobster 308, i.e., the same slope for lobsters of different weights may indicate a different physical characteristic. The weight scale may be included as part of the grader 316, for instance.

In some embodiments, an RFID tag (not shown) storing information related to the ID of the lobster 308 is attached to the lobster and the sensor 300 is part of an RFID device that includes an electromagnetic resonant circuit that is loaded by the lobster 308 as it passes over the sensor 300.

In some embodiments, the controller is operable to estimate a physical characteristic of the lobster 308 based on the loading effect of the lobster on the electromagnetic resonant circuit of the sensor 300 and store the information relating to the estimated physical characteristic on the RFID tag by transmitting the information to the RFID tag, via the electromagnetic resonant circuit of the sensor 300, for storage on the tag in addition to the information already stored on the tag related to the ID of the lobster and/or transmitting the information to the server 320 for storage in the database 326.

In some embodiments, the controller 302 reports the slope and/or the estimate of the physical characteristic and/or the raw resonant measurements, i.e., $F_{resonant\_ref}$, $A_{resonant\_ref}$, $F_{resonant\_min}$ and $A_{resonant\_min}$ for each lobster 308 to the server 320 through the hub 322 via the input/output at 334 and the output at 336. Each lobster 308 may be assigned a lot and bin number by the grader 316, and the lot and bin number may also be communicated to the server 320. The listener block 324 receives the data from the output at 336 of the hub 322 and stores the data in the database 326 through its output at 338.

In some embodiments, the database 326 is a MySQL database.

The data in the database 326 can be accessed by the remote user system 330 on the internet via the interface 328 using the input/output 344.

In some embodiments, the remote user system 330 can also send instructions to the controller 302 through the interface 328 and the hub 322 via the input/output 344, the output 342 and the input/output 334.

In some embodiments, the controller 302 is implemented as a personal computer with a central processing unit (CPU) card, an Ethernet card, and analog card, a power regulator card, and a custom processing card.

The Ethernet card provides an Ethernet interface from the controller to the other Ethernet devices in the system, and allows for remote control of the controller 302.

The analog card provides an interface between the digital CPU card and the sensor 300 in embodiments in which an analog sensor is implemented. The analog card converts a digital number to an analog voltage and vice-versa. It may also have optically isolated digital inputs for optical gate signals, such as the output of the trigger 306, and mechanical relays for switching LEDs or gating power to equipment. The analog card is controlled by embedded code to indicate when a trigger has occurred, to output an analog drive signal to the custom card, and measure the analog response from measurement circuitry on the custom card. The mechanical relays may be used to light the LEDs if a fault condition exists and to gate power to the custom card.

The power regulator card provides conditioning and regulation of input power from an external DC source. This card allows the input voltage to vary from 6 VDC to 36 VDC without affecting the processes running in some embodiments. It also provides robustness to power line noise.

In some embodiments, the custom card may contain a varactor-controlled oscillator and measurement circuitry of the custom card may be implemented as a vector volt meter (VVM). Changing the analog drive signal voltage applied to the varactor, such as by applying a saw-tooth-like analog waveform, modifies the frequency of the drive oscillator. The VVM measures the relative magnitudes of the input and the output at 312 of the sensor 300, and, in some embodiments, their relative phase. A digital to analog interface card that is capable of generating the plurality of analog excitation frequencies to be applied to the input of the sensor 300 may also be provided in the controller 302.

In some embodiments, the custom card includes a multi-frequency chip, such as a direct digital synthesis digital-to-analog converter (DDS DAC) that is capable of receiving a multi-bit digital input and generating a specific frequency for each multi-bit input. In general, any analog signal source may be used for generating a plurality of excitation frequencies that will encompass the loaded and unloaded resonant peaks of the sensor 300.

In some embodiments where a varactor controlled oscillator is used in the controller 302, a "saw-tooth-like" wave form may be used to drive the varactor, so that the excitation frequency of the input at 312 of the sensor 300 is repeatedly "swept" over a specific range of frequencies.

The processing capability of the controller 302 may be implemented using a CPU, an application specific integrated circuit (ASIC) or a logic device such as a field programmable gate array (FPGA) or a programmable logic device (PLD). In general, the processing capability of the controller 302 might be implemented using hardware, software, firmware or combinations thereof.

Varactors are generally highly non-linear, and therefore a multi-frequency chip may offer better performance than the varactor-based implementations, since the output frequency of the multi-frequency chip can be accurately controlled by its digital inputs.

In some embodiments, the biologist station console 332 allows a biologist or other qualified technician or user to enter pertinent biological data from sampled lobsters, which data can then be sent to and stored in the database 326. The biological data may include a refractive index from a sampled lobster, which can provide continuous calibration data for the sensor 300. For example, if the refractive index of a sampled lobster is determined by another system or device (not shown) and entered into the database 326 by a biologist using the biologist station console 332 on the processing line, the sampled lobster can then be placed on the belt 304 and passed over the sensor 300 as a calibration lobster so that the physical characteristic estimation algorithm executed by the controller 302 can be adjusted to correspond to the refractive index determined by the biologist if there is any discrepancy.

The biologist is also able to view results and reports from the interface 328 from the biologist station console 332.

In some embodiments, much of the processing done by the controller 302 is carried out by a 32 bit commercially available processor. This processor is in control of all of the frequency scanning requirements of the system. This change allows control of a 32 bit digital frequency oscillator chip, i.e. a multi-frequency source such as a controlled oscillator, through Serial Peripheral Interface (SPI) communications.

The frequency oscillator chip might have the ability of generating sinusoidal voltage outputs from DC (0 Hz) to approximately 70 MHz in 0.04 Hz steps, for example. Such a chip could replace the varactor-controlled oscillator of the system described above as a means of having a more broad frequency sweeping capability and more accurate control over the specific operating frequency of the sensor 300.

The processor could also be used to read the VVM output voltages (phase and magnitude outputs), with a 16 bit 500 kSPS analog to digital converter (ADC) over the SPI interface, for instance.

When such a processor is used, the CPU card of the controller 302, which used to do all of the system processing, now serves primarily as the network communications router for the system. However, the CPU card can still be used to run data mining models on the measured values returned from the processor as well as the grader 316 system. This will be explained in more detail below.

At boot, or during idle time, the processor may do a wide range frequency sweep of the current operating conditions to determine exactly where the resonant peak of the sensor 300 is located (in frequency). It does this by commanding the frequency oscillator chip to start at a 15 MHz frequency and step all the way to 25 MHz in 1.5 kHz steps in one embodiment. During this sweep, the voltage output of the VVM is monitored in order to locate the highest magnitude value. The largest magnitude of the entire sweep is detected as the resonant peak of the sensor 300.

After the initial air sweep the processor will wait until the controller 302 detects a trigger from the trigger 306. When the controller 302 detects this event it informs the processor of the presence of an approaching lobster 308 on the belt 304, illustratively via a TCP connection. The processor then performs a 1.5 MHz sweep centered around the resonant peak in 18.75 kHz steps. This accurately detects the frequency of the resonant peak in "air" (no lobster present).

The processor centers its frequency window about this peak frequency and starts its scanning. The scan may consist of a fixed number of frequency sweeps (illustratively ~80), over which the VVM voltages are measured at multiple identical frequency values (illustratively ~100 frequency values per sweep). This data could be stored in local memory of the processor during each sweep. If the specific lobster 308 that is being scanned is detected as a calibration lobster (based on a triggering event from the biologist station console 332), the entire sweep data is transmitted, again illustratively via TCP, to the Listener 324 to be stored in the database 326 for future analysis. On regular lobsters (non-calibration), a delay equal to the length of the TCP transmit time can be added at the end of each sweep so that the measurement results are similar between calibration lobsters and non-calibration lobsters.

When a scan is completed, and before transmitting data over TCP or during the delay, the processor may command the frequency oscillator chip to set the frequency back to the initial frequency of the sweep range. This is done to help avoid issues of the system instantaneously changing from a high frequency to a low frequency at the start of each sweep.

While sweeping, the processor computes a moving average filter, illustratively a five point filter, on the data to clean it up and determine a more accurate peak location for the current sweep. These peak values can be stored in an array in memory for later processing. When the scan is complete and all of the peak locations of each sweep have been stored in memory, the processor calculates all statistics to be used in the slope algorithm. Once these statistics are computed the processor computes the actual slope value defined by (1). Finally, the processor may send all of the calculated statistic values and the slope value to the listener 324 and they are stored in the database 326.

Once a lobster activates the trigger 306, the controller 302 notifies the processor possibly with a TCP communication. When the processor has finished scanning, it returns the calculated values to the controller 302. The controller 302 keeps this data in memory until it has received the weight information from the grader 316 in some embodiments. Once the weight information is received, the controller 302 takes all of the combined data that it has received about this lobster and runs it through a data mining model to get an estimate of RI.

Based on this estimate, the controller 302 may give the lobster a classification value and send that value to the grader 316 so that it may be placed in the correct bin.

If the current lobster was determined to be a calibration lobster, based on an input from the biologist station console 332 communications and a timing window for instance, the controller 302 conducts further processing after the transmission to the grader 316 is completed. Since the lobster is a calibration lobster, the controller 302 knows its measured RI value (transmitted from the biologist station console 332). The controller 302 attaches this value to the other measured statistics and adds it to a global array of a previous number of lobster calibration data. The controller 302 then executes its data mining code on this global array to update the current data mining model. All subsequent lobsters that are scanned have their quality judged based on this current model (which changes once a new calibration lobster is entered).

An example of a data mining algorithm that may be used in accordance with an embodiment of the present invention is a Stochastic Gradient Boosting algorithm, as described in Jerome H. Friedman, "Stochastic Gradient Boosting", Computational Statistics & Data Analysis, v. 38 n. 4, p. 367-378, 28 Feb. 2002.

In some embodiments, the data mining algorithm may be trained using only a subset of all of the data collected from calibration lobsters. For example, only the last 100 calibration lobsters may be used to train the algorithm. This may allow the model to track changes over time. The selection of the size of the training "window", e.g. 100 lobsters, is an implementation specific window. Statistical analysis on past data, for example, a previous season's entire data set, may be used to optimize the size of the training window.

An embodiment of the sensor 300 is shown in detail in FIG. 4. In the embodiment shown in FIG. 4, the sensor 300 includes two substantially co-planar plates 406,408, an inductor 404, a "tickler" coil 400 and a "sense" coil 402.

The two co-planar plates 406,408 are located a short distance apart and function as a planar capacitor. The two co-planar plates 406,408 are respectively connected to the ends of the inductor 404, which is shown as a coil inductor in FIG. 4.

The "tickler" coil 400 is located at one end of the inductor 404 and the "sense" coil 402 is located at the other end of the inductor 404 so that the "tickler" coil and the "sense" coil are inductively coupled to the inductor 404.

The "tickler" coil 400 is connected to the input 311 of the sensor 300 and the "sense" coil 402 is connected to the output 313 of the sensor 300. The input 311 and the output 313 are shown in FIG. 3 as a single connection 312.

The components of the sensor 300 shown in FIG. 4 form a resonant tank circuit that will have a specific resonant peak in air that depends on the dimensions and properties of the individual components. The design of such a circuit to have a desired resonant characteristic will be apparent to those skilled in the art.

In operation, when an excitation frequency is applied to the input 311, the "tickler" coil 400 couples the excitation frequency to the inductor 404 and the frequency response of the tank circuit is coupled to the "sense" coil 402, and hence to the output 313 of the sensor 300. The output 313 of the sensor will be at a peak when the excitation frequency is equal to the resonant frequency of the tank circuit. For example, see the resonant peak 200 in FIG. 2. The two co-planar plates 406, 408 function as a planar capacitor, and therefore an electric field is generated between the two plates. This electric field extends above the upper surface of the co-planar plates 406, 408, and when a lobster passes above the sensor it will interact with this electric field. This interaction will effectively load the tank circuit with the impedance of the lobster and the resonant peak of the tank circuit will change as described above with reference to FIG. 2.

In some embodiments, the two co-planar plates are implemented with aluminum plates that are ⅛" thick, four inches long and 18 inches across. The plates 406,408 are arranged so that they are separated by a constant one inch gap along one of their long edges. The plates 406,408 are arranged above the inductor 404 and the plates 406,408 and the inductor 404 are mounted in a high density polyethylene (HDPE) platform that can be installed under the processing belt 304 shown in FIG. 3.

In some embodiments, the inductor 404 is implemented with a coil with a diameter of approximately 2.25 inches and a length of approximately 6.5 inches with nine turns. The coil may be mounted in a sealed canister, with the "tickler" coil 400 and "sense" coil 402 located within the sealed canister.

The inductor 404 and the plates 406,408 form a resonant tank with a very high quality factor Q. For example, the Q of the tank circuit may be 150 to 200.

In some embodiments, the resonant peak of the tank circuit is close to 20 MHz in air.

While the foregoing embodiments have been described in the context of non-contact measurements, i.e., embodiments in which remote loading of an electromagnetic resonant circuit by a seafood product is used to estimate a physical characteristic of the seafood product, embodiments are not limited to non-contact measurements, nor are they necessarily limited to estimation based on loading effect of the seafood product on an electromagnetic resonant circuit.

In some embodiments, a sensor comprising a plurality of plates or other forms of probe may be brought into direct contact with a seafood product, for example, on the underside of a tail of a lobster. A first one of the probes may be driven with a test signal and the received test signal at one or more of the other probes may be measured. The received test signals at the one or more other probes may then be used to estimate a physical characteristic of the seafood product.

Contact of an electromagnetic resonant circuit with a seafood product may cause the "squashing" of a resonant peak of the electromagnetic resonant circuit, making resonant circuits potentially unsuitable for some contact measurement-based embodiments. Accordingly, non-resonant circuits may be used in some contact measurement-based embodiments to generate the test signal(s) used to drive the probes that are contacted to the seafood product.

In some embodiments, the relative magnitude and phase between the test signal driven to the first probe and the test signals received at the one or more other probes are measured, thus detecting the relative impedance of the lobster tissue occupying the space between the drive probe and each sense probe. By combining the results of the measurements made for each individual probe, a profile of the impedance of the local tissue below the contact points of the probes can be determined. By using a plurality of probes contacted on, for example, the underside of a lobster tail, the profile of the impedance of the local tissue depicts an "image" of the water-to-tail muscle in that region. For post-molt lobsters, this profile may depict significant water content between the two tail muscles, and thus a steep gradient in this profile curve. The gradient may not be as significant in the case of pre-molt lobsters in which typically very little inter-muscle water exists. Thus, the gradient in these water-to-tail muscle profiles may be used as a method to discern meat yield content in the lobster.

While the foregoing embodiments have been described in the context of measurement of individual seafood products, such as lobsters, embodiments are not limited to determining the physical characteristics of individual lobsters.

In some embodiments, the measurement system 350 may be implemented in a crate sensor form factor. That is, the measurement system 350 may be used to determine the average physical characteristic, for example meat yield, of a crate containing multiple specimens of a particular seafood product, such as lobster. For example, in some embodiments, the plates 406, 408 in the embodiment shown in FIG. 4 may be implemented as "U-shaped" plates with three substantially planar surfaces, and a crate of seafood product may be placed in the open well of the "U" for measurement. In such an embodiment, each crate of seafood product may be placed into the U-shaped sensor arrangement by hand or any other mechanism, and the sensor could be used wharf-side to evaluate the physical characteristics of crates of seafood product that are available.

Evaluating a physical characteristic of a crate of seafood product may allow a seafood processor to select the "grade" of seafood product that they are interested in purchasing, rather than having to purchase a crate of seafood product and then individually evaluate each lobster, although a crate scanner might be used for initial selection of a group of products for purchase, and those product could be processed individually by an online scanning system for specific sorting.

Figure 5:
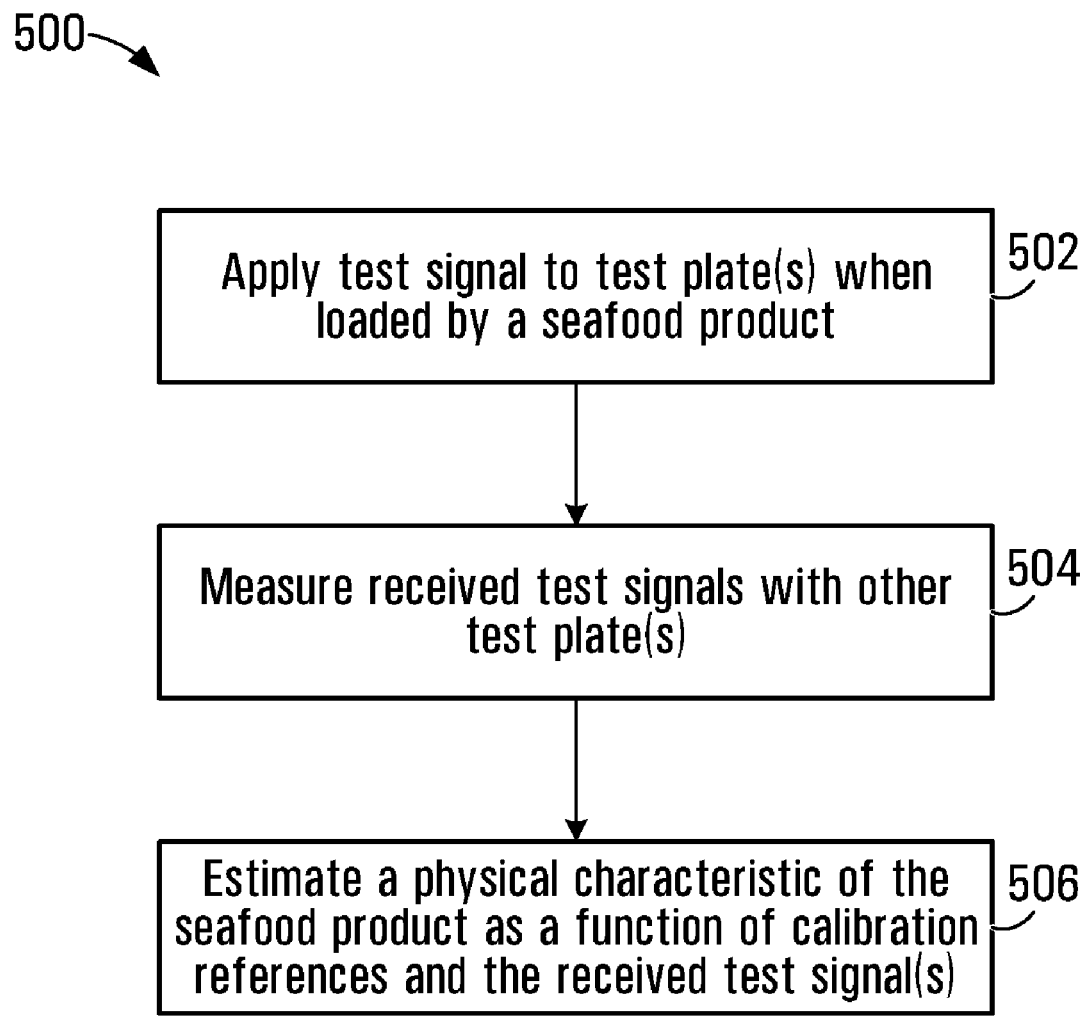
FIG. 5 is a flowchart of an example of another method in accordance with an embodiment of the invention.

While the sensor 300 described above with reference to FIG. 4 is a resonant circuit with two co-planar plates 406, 408, embodiments are not limited to resonant sensor arrangements with only two plates. For example, a method 500 in accordance with an embodiment will now be described with reference to the flowchart shown in FIG. 5, in which a sensor with multiple plates is used to determine a physical characteristic of a crate of seafood product.

Method 500 begins at step 502, in which a test signal is applied to one or more of a plurality of spatially separated plates while the plates are loaded by a seafood product, which may be a crate containing multiple specimens of a particular seafood product, such as lobster.

In step 504, received test signals are measured at another plate, illustratively at two or more of the other plates.

In step 506, a physical characteristic of the seafood product, e.g. an average meatedness of the crate of lobster, is estimated as a function of calibration references, which might be determined while the plates are not loaded by a seafood product, and the received test signals in the loaded state. Differences between the measured signals and the reference signals may be used to distinguish between different grades.

Figure 6:
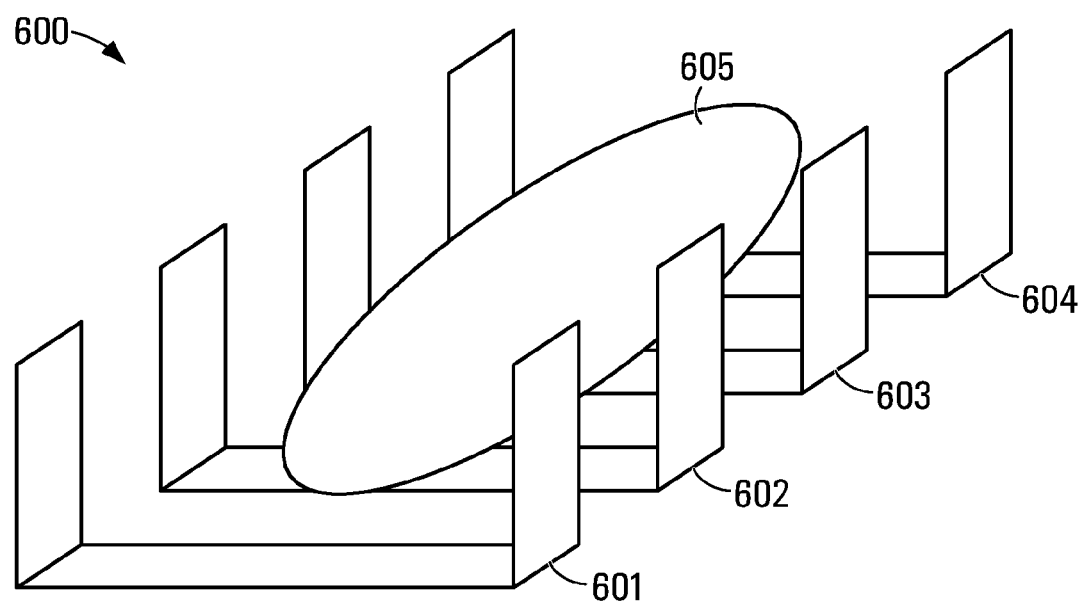
FIG. 6 is a schematic of an electromagnetic circuit in accordance with an embodiment of the invention.

FIG. 6 is a schematic of a multi-plate electromagnetic sensor circuit 600 in accordance with an embodiment of the present invention. The sensor circuit 600 may be used, for example, with the method illustrated in the flowchart of FIG. 5.

Sensor circuit 600 includes four spatially separated plates 601, 602, 603, 604 that are "U-shaped" and arranged to define a volume into which a crate of seafood product, generally represented at 605, can be placed for measurement.

The operation of the sensor circuit 600 uses the principle of assessing the physical properties of objects by measuring disturbances in an EM field caused by the presence and positioning of these objects within the EM field.

The sensor circuit 600 may be controlled by a controller (not shown) that is similar to the controller 302 illustrated in FIG. 3.

The controller creates radio-frequency (RF) oscillations for driving the plates 601, 602, 603, 604 and detects changes in the received RF signal at the plates due to the EM field disturbance caused by the crate of seafood product 605.

In some embodiments, the plates 601, 602, 603, 604 are surrounded on their outer periphery by an outer shell (not shown) that acts as shield so that the EM field generated by applying test signals to the plates is generally confined to the volume defined by the plates. In these embodiments, the plates 601, 602, 603, 604 might be mounted inside the shield on non-conducting standoffs that provide galvanic isolation between the shield and the plates. The plates are spaced apart and, in some embodiments, have rollers positioned between them to provide support for the crate of seafood product 605.

By using multiple plates 601, 602, 603, 604, it is possible to measure different depths into the crate 605. For example, by driving and measuring from neighboring plates (for example driving 601 and sensing on 602), the EM field generated may penetrate only a shallow amount into the crate 605 (for example, measuring lobsters near the bottom of the crate). However, by driving the end plate 601 and sensing from the plate 604 at the opposite end of the sensor 600, the field penetration is deeper into the crate 605 (for example, measuring lobsters closer to the top of the crate).

The disturbance in the EM field is detected by comparing the signals from the sensing plate in unloaded and loaded states. In both cases the drive signal can be taken as a reference. In some embodiments, a Vector Volt Meter (VVM) is used to measure the driven and sensed signals. The drive signal is fed to one of the inputs of the VVM while the sense signal is fed to another input of the VVM. The VVM has two output analog voltage signals that represent the difference in magnitude and phase between its two input signals, thus qualifying the impedance of the tested object.

In some embodiments, driving and sensing with the plates 601, 602, 603, 604 may be done over a range of frequencies. For example, test signals with frequencies from 1 KHz to 50 MHz in steps of 5 KHz may be used in some embodiments.

In one particular embodiment, the controller (not shown) includes a main board (MB) that provides a digital communication interface with, for example, a remote data server, and an analog board (AB) that interfaces with the main board and the plates 601, 602, 603, 604 to drive and sense radio frequency signals using the plates.

In some embodiments, the MB passes digital data containing a requested test frequency to the AB via a serial peripheral interface (SPI) bus. A Direct Digital Synthesis Digital-to-Analog Converter (DDS DAC) receives the data and produces the RF signal that is further amplified and fed to one of the plates (for example plate 601) to produce an EM field in the sensor's test space, i.e. inside the volume defined by the plates). The field can be sensed by any of the other plates (for example, plate(s) 602, 603 and/or 604) of the sensor 600 with the exception of the one that is being driven at the moment.

In some embodiments, the VVM outputs are converted to digital form in a high-speed Analog-to-Digital Converter (ADC). The digital data containing results (magnitude and phase) of the scan for the current frequency is sent then to the MB via an SPI bus. In one embodiment, the MB runs software to store and analyze the scan data. The controller (not shown) may also include a display that indicates the result of the scan. For example, the controller may include a visual display that indicates the average meatedness of the seafood product in the crate 605.

Control of both EM field frequency and the drive-sense plate spacing may allow the impedance of a test object, for example a crate of seafood product, to be analyzed at different frequencies and at different penetration depths.

In some embodiments, the following pattern of driving and sensing is used:

Drive 601
  Sense 602
  Sense 603
  Sense 604
Drive 602
  Sense 601
  Sense 603
  Sense 604
Drive 603
  Sense 601
  Sense 602
  Sense 604
Drive 604
  Sense 601
  Sense 602
  Sense 603

The foregoing pattern results in multi-frequency graphs (for example, 1 KHz to 50 MHz) for each "pair" of driven/sense plate arrangements.

In some embodiments, the magnitude of the sensed signals is used over a broad frequency range to discern the quality grade of a crate of seafood product. For example, in some embodiments, the difference in magnitude of the sensed signals in an unloaded and loaded state is used to distinguish between crates of high quality and low quality lobsters.

While the plates 601, 602, 603, 604 are shown as U-shaped plates in FIG. 6, more generally a plurality of plates of any shape may be utilized to define a volume into which a crate can be placed for measurement. For example, each of the "arms" of the plates 601, 602, 603, 604 might not be connected to one another so that each plate is separated into three separate plates (a top or bottom and two sides) that may be driven and sensed independently of one another.

In some embodiments, one or more of the plates might be movable to "scan" different portions of the crate 605. For example, in one embodiment, there may be one or more fixed plates and one or more movable plates. In one particular embodiment, only one fixed plate and one movable plate are used.

While the foregoing embodiments utilize changes in the amplitude of the electromagnetic response of resonant and non-resonant circuits to estimate a physical characteristic of a seafood product, other differences in the electromagnetic response of resonant or non-resonant circuit may be used in some embodiments. For example, some embodiments, may use the phase of the electromagnetic response, rather than, or in addition to, the amplitude.

While the foregoing has been provided in the general context of determining a physical characteristic such as meat yield of lobsters, embodiments of the present invention are also applicable to other crustaceans, and can be applied to determining a physical characteristic of any product in which perceived quality is at least partially a function of water content, and more particularly intracellular vs. extracellular water content.

What has been described is merely illustrative of the application of the principles of the invention. Other arrangements and methods can be implemented by those skilled in the art without departing from the present invention.

The invention claimed is:

1. A method comprising:
    determining, by a controller, a minimum peak resonant frequency $F_{resonant\_min}$ and peak resonant amplitude $A_{resonant\_min}$ at $F_{resonant\_min}$ of an electromagnetic resonant circuit when loaded by a seafood product; and
    estimating, by the controller, a physical characteristic of the seafood product based on a slope defined by:

$$(A_{resonant\_ref} - A_{resonant\_min})/(F_{resonant\_ref} - F_{resonant\_min}),$$

where $F_{resonant\_ref}$ is a reference peak resonant frequency of the electromagnetic resonant circuit in an unloaded state, and $A_{resonant\_ref}$ is a reference peak resonant amplitude of the electromagnetic resonant circuit in the unloaded state.

2. The method according to claim 1, further comprising:
    determining the reference peak resonant frequency $F_{resonant\_ref}$ and the reference peak resonant amplitude $A_{resonant\_ref}$ of the electromagnetic resonant circuit in the unloaded state.

3. The method according to claim 2, wherein determining $F_{resonant\_ref}$ and $A_{resonant\_ref}$ comprises:
    applying a plurality of excitation frequencies to the electromagnetic resonant circuit in the unloaded state;
    measuring an amplitude of an output of the electromagnetic resonant circuit for each one of the excitation frequencies;
    determining $A_{resonant\_ref}$ as a peak amplitude of the measured amplitudes; and determining $F_{resonant\_ref}$ as the excitation frequency corresponding to the peak amplitude of the measured amplitudes.

4. The method according to claim 2, wherein determining $F_{resonant\_ref}$ and $A_{resonant\_ref}$ comprises:
maintaining a record of peak resonant amplitudes and frequencies in previous unloaded states;
applying a plurality of excitation frequencies to the electromagnetic resonant circuit in the current unloaded state;
measuring an amplitude of an output of the electromagnetic resonant circuit for each one of the excitation frequencies;
determining $A_{resonant\_ref}$ as a rolling average of a number of the peak resonant amplitudes of the previous unloaded states and the peak amplitude of the current measured amplitudes; and
determining $F_{resonant\_ref}$ as a rolling average of a number of the peak resonant frequencies of the previous unloaded states and the peak resonant frequency of the current measured amplitudes corresponding to the peak amplitude of the current measured amplitudes.

5. The method according to claim 1, further comprising:
determining a weight of the seafood product,
wherein estimating the physical characteristic comprises estimating the physical characteristic based on the slope and the weight of the seafood product.

6. The method according to claim 1, further comprising:
maintaining a database of $A_{resonant\_ref}$, $A_{resonant\_min}$, $F_{resonant\_ref}$ and $F_{resonant\_min}$ for each seafood product.

7. The method according to claim 6, further comprising:
maintaining the estimated physical characteristic for each seafood product in the database.

8. The method according to claim 1, further comprising:
performing linear regression on the slope to determine a linear relationship between the slope and the physical characteristic.

9. The method according to claim 1, further comprising:
determining a threshold as a boundary between quality grades; and
determining a quality grade of the seafood product by comparing the slope to the threshold.

10. The method according to claim 9, wherein determining the threshold comprises performing a data mining algorithm.

11. The method according to claim 1, further comprising:
calibrating by:
determining a slope for a calibration seafood product with a known physical characteristic; and
adjusting a function for estimating the physical characteristic based on any discrepancy between the known physical characteristic and the physical characteristic estimate based on the determined slope.

12. The method according to claim 1, wherein the seafood product comprises a plurality of specimens.

13. The method according to claim 12, wherein the plurality of specimens are contained in a crate.

14. The method according to claim 1, further comprising:
reading an ID from a Radio Frequency Identification (RFID) tag associated with the seafood product with the electromagnetic resonant circuit; and
associating the ID of the RFID tag associated with the seafood product with information relating to the estimation of the physical characteristic of the seafood product.

15. The method according to claim 14, wherein associating the ID of the RFID tag associated with the seafood product with information relating to the estimation of the physical characteristic of the seafood product comprises at least one of:
transmitting, via the electromagnetic resonant circuit, information relating to the estimation of the physical characteristic of the seafood product to the RFID tag associated with the seafood product for storage on the RFID tag; and
storing the information relating to the estimation of the physical characteristic of the seafood product in a database, such that the information is associated with the ID of the RFID tag.

16. The method according to claim 15, further comprising:
reading the RFID tag associated with the seafood product to retrieve the information relating to the estimation of the physical characteristic of the seafood product associated with the RFID tag; and
sorting the seafood product into one of at least two grades based on the information retrieved from the RFID tag.

17. A system comprising:
a sensor comprising an electromagnetic resonant circuit;
a controller, functionally connected to the electromagnetic resonant circuit, that:
determines a minimum peak resonant frequency $F_{resonant\_min}$ and peak resonant amplitude $A_{resonant\_min}$ at $F_{resonant\_min}$ of the electromagnetic resonant circuit when the electromagnetic resonant circuit is loaded by a seafood product; and
estimates a physical characteristic of the seafood product based on a slope defined by:

$$(A_{resonant\_ref} - A_{resonant\_min})/(F_{resonant\_ref} - F_{resonant\_min}),$$

where $F_{resonant\_ref}$ is a reference peak resonant frequency of the electromagnetic resonant circuit in an unloaded state, and $A_{resonant\_ref}$ is a reference peak resonant amplitude of the electromagnetic resonant circuit in the unloaded state.

18. The system according to claim 17, wherein the controller also determines the reference peak resonant frequency $F_{resonant\_ref}$ and the reference peak resonant amplitude $A_{resonant\_ref}$ of the electromagnetic resonant circuit in the unloaded state.

19. The system according to claim 18, wherein the controller comprises a variable frequency source, and wherein the controller determines $F_{resonant\_ref}$ and $A_{resonant\_ref}$ by:
controlling the variable frequency source to apply a plurality of excitation frequencies to the electromagnetic resonant circuit in the unloaded state;
measuring an amplitude of an output of the electromagnetic resonant circuit for each one of the excitation frequencies;
determining $A_{resonant\_ref}$ as a peak amplitude of the measured amplitudes; and
determining $F_{resonant\_ref}$ as the excitation frequency corresponding to the peak amplitude of the measured amplitudes.

20. The system according to claim 17, further comprising:
a weight scale, functionally connected to the controller, that determines a weight of the seafood product,
wherein the controller estimates the physical characteristic based on the slope and the weight of the seafood product.

21. The system according to claim 17, wherein the controller:
maintains a record of peak resonant amplitudes and frequencies in previous unloaded states;

determines $A_{resonant\_ref}$ as a rolling average of a number of the peak resonant amplitudes of the previous unloaded states and the peak amplitude of the current measured amplitudes; and determines $F_{resonant\_ref}$ as a rolling average of a number of the peak resonant frequencies of the previous unloaded states and the peak resonant frequency of the current measured amplitudes corresponding to the peak amplitude of the current measured amplitudes.

22. The system according to claim 17, further comprising:
a server having a database in communication with the controller,
wherein the controller stores a record in the database of the estimated physical characteristic, $A_{resonant\_ref}$, $A_{resonant\_min}$, $F_{resonant\_ref}$ and $F_{resonant\_min}$ for each seafood product.

23. The system according to claim 17, wherein the electromagnetic resonant circuit comprises:
two substantially co-planar plates separated by a gap;
an inductor having a first end and a second end respectively functionally connected to the two substantially co-planar plates;
a tickler coil inductively coupled to the inductor; and
a sense coil inductively coupled to the inductor,
wherein the controller applies a plurality of excitation frequencies to the tickler coil and determines $F_{resonant\_min}$ and $A_{resonant\_min}$ based on an output of the sense coil when the electromagnetic resonant circuit is loaded by the seafood product.

24. The system according to claim 17, further comprising:
a biologist station console functionally connected to the controller, the biologist station console allowing a user to enter a known physical characteristic of a calibration seafood product,
wherein the controller:
determines a slope for the calibration seafood product with the known physical characteristic; and
adjusts a function for estimating the physical characteristic based on any discrepancy between the known physical characteristic and the physical characteristic estimate based on the determined slope.

25. The system according to claim 17, wherein the electromagnetic resonant circuit comprises three or more substantially planar plates separated by gaps.

26. The system according to claim 25, wherein the three or more substantially planar plates define a volume.

27. The system according to claim 17, wherein the seafood product comprises a plurality of specimens.

28. The system according to claim 17, wherein the electromagnetic resonant circuit is part of a Radio Frequency Identification (RFID) reader.

29. The system according to claim 28, wherein the controller is configured to perform at least one of the following steps:
transmit, via the electromagnetic resonant circuit, information relating to the estimation of the physical characteristic of the seafood product to an RFID tag associated with the seafood product; and
store the information relating to the estimation of the physical characteristic of the seafood product in a database, such that in the database the information is associated with an ID of the RFID tag associated with the seafood product.

30. The system according to claim 29, further comprising:
a second RFID reader comprising a second electromagnetic resonant circuit configured to read the RFID tag associated with the seafood product to retrieve the information relating to the estimation of the physical characteristic of the seafood product; and
a grader, functionally connected to the RFID reader, configured to sort the seafood product into one of at least two grades based on the information retrieved from the RFID tag.

31. The system according to claim 30, wherein the information relating to the estimation of the physical characteristic of the seafood product comprises a grade of the seafood product, and wherein sorting the seafood product comprises sorting the seafood product based on the grade of the seafood product stored on the RFID tag.

* * * * *